US006024919A

United States Patent [19]

Nelson et al.

[11] Patent Number: 6,024,919

[45] Date of Patent: Feb. 15, 2000

[54] SONIC TREATMENT TO SELECTIVELY REDUCE THE VOID VOLUME OF SINTERED POLYMERS

[75] Inventors: Eric M. Nelson, San Clemente; Todd C. White, San Diego, both of Calif.

[73] Assignee: LXN Corporation, San Diego, Calif.

[21] Appl. No.: 09/006,787

[22] Filed: Jan. 14, 1998

[51] Int. Cl.[7] .................... G01N 33/48

[52] U.S. Cl. .................... 422/58; 422/56; 436/169; 436/63

[58] Field of Search .................... 264/603, 442; 422/56, 57, 58, 61, 100–101, 102; 436/168, 164, 169, 63

[56] References Cited

U.S. PATENT DOCUMENTS

| | | | |
|---|---|---|---|
| 4,300,910 | 11/1981 | Pannwitz . | |
| 5,470,752 | 11/1995 | Burd et al. | 436/87 |
| 5,597,532 | 1/1997 | Connolly | 422/58 |
| 5,639,672 | 6/1997 | Burd et al. | 436/525 |
| 5,695,949 | 12/1997 | Galen et al. | 435/14 |

FOREIGN PATENT DOCUMENTS

| | | |
|---|---|---|
| WO 96/31270 | 10/1996 | WIPO . |

*Primary Examiner*—Lyle A. Alexander
*Attorney, Agent, or Firm*—Campbell & Flores LLP

[57] ABSTRACT

The present invention provides a method of sonic treatment to selectively reduce the void volume of a sintered polymer such as porous high density polyethylene (HDPE). The invention also provides a method and an article of manufacture for receiving a liquid sample, where a first portion of the sintered polymer (1*a*) overlies a solid surface (4*a*) and a second portion of the polymer (1*b*) overlies a window (4*b*). Sonic treatment of the sintered polymer reduces the void volume of the first portion (1*a*) compared to the second portion (1*b*). As a result, a liquid sample applied to the polymer will preferentially migrate through the second portion (1*b*), rather than through the first portion (1*a*). When the article of manufacture is used to analyze a liquid sample such as blood, less sample is required because of the preferential migration in the sonically treated sintered polymer.

13 Claims, 3 Drawing Sheets

SONIC TREATMENT TO SELECTIVELY REDUCE THE VOID VOLUME OF SINTERED POLYMERS

BACKGROUND OF THE INVENTION

1. Field of the Invention

The present invention generally relates to methods for altering the physical properties of materials and, more specifically, to methods for sonically treating sintered polymers to selectively reduce their void volume.

2. Background Information

Various assays are available to monitor medical conditions at home or in a clinical setting. Such assays often use chemically treated test strips that can react with specific analytes in the body fluids of patients. For example, blood glucose levels can be monitored using test strips that react with glucose in blood samples, causing a color change on the strips. By observing the degree of color change, patients under a diabetes-management regimen can monitor their glucose levels. If the levels are abnormally high, they can then take appropriate steps such as diet management or self-administration of insulin. Failure to monitor glucose levels can result in high glucose levels, leading to cardiovascular disease and degeneration of the kidneys, retinas and nervous system.

When using a test strip device, sufficient sample must be applied to ensure an accurate result. If insufficient sample is applied, the reaction may fail or react incompletely, yielding a misleading measurement. Even when sufficient sample is applied to the strip, it may not absorb the sample at once, leaving a pool of liquid to rest until eventually absorbed. Until the sample is completely absorbed, it risks being spilled or scattered by inattentive handling of the device, which can also result in a misleading measurement.

Previous devices have sought to speed the absorption of liquid samples by providing a porous layer over the test strip. When the sample is applied to such a layer, the porous structure allows relatively quick absorption so that a pool of sample does not remain on the surface for long. As the sample is absorbed, it passes through the pores by capillary action until it reaches the test strip underneath. Thus, the layer can be said to be a "receiving layer" for absorbing the liquid sample and allowing it to migrate to the test strip.

Unfortunately, a larger volume of sample is needed when using such a receiving layer. Because a certain amount of sample is retained in the pores of the receiving layer, the sample never completely migrates to the test strip. Instead, a significant fraction of the sample can spread to peripheral areas of the receiving layer, where it is retained in the pores. Unless larger volumes of sample are applied the receiving layer, the test strip may not receive sufficient sample to yield an accurate measurement. Thus, while a receiving layer speeds absorption of the sample and reduces spillage, this benefit is partially offset by requiring the application of larger sample volumes.

Applying larger samples of body fluids is practicable when the sample is easy to obtain, for example with urine or saliva, but it can be problematic when obtaining the sample is difficult or painful. When the sample to be tested is blood, the sample is typically obtained by puncturing the skin and then pressing the skin to apply drops to the test strip device. If insufficient blood is produced, the patient must repuncture the skin until sufficient blood is obtained to yield an accurate measurement from the test strip device. Obtaining sufficient blood for testing can therefore be difficult when patients have poor circulation and can be especially traumatic with young patients. Thus, the need to obtain larger samples of blood can deter patients from regularly using test strip devices, leading to ineffective compliance with their disease-management regimens.

Thus, there is a need for a layer for receiving a liquid sample where the retained volume is reduced, thereby minimizing the amount of sample necessary. The present invention satisfies this need and provides related advantages as well.

SUMMARY OF THE INVENTION

The present invention provides a method for selectively reducing the void volume of a sintered polymer by sonic treatment. The sonic treatment is effective under a variety of conditions, for example between 15 and 50 kHz and between 10 and 1000 Joules per cubic centimeter of polymer, depending on the composition, shape and arrangement of the sintered polymer.

Useful sintered polymers include polypropylene, polyvinylidene fluoride, ethylenevinyl acetate, styreneacrylonitrite, polytetrafluoroethylene and related copolymers. A particularly useful sintered polymer is porous high density polyethylene (HDPE). HDPE and other sintered polymers have pores in a range of effective diameters, such as between 5 and 300 microns. Such sintered polymers are also useful in a variety of shapes, such as in the form of substantially planar sheets.

The void volume can be differentially reduced by immobilizing the sintered polymer against a solid during sonic treatment. In particular, a first portion of the sintered polymer can be immobilized against a solid during sonic treatment, while a second portion is not. For example, the second portion can overlie a window in the solid, so it is not immobilized during the sonic treatment. As a result of the arrangement, the void volume of the first portion becomes less than in the second portion.

The invention also provides an article of manufacture for receiving a liquid sample, where a first portion 1*a* of a sintered polymer overlies a solid 4*a* and a second portion 1*b* of the sintered polymer overlies a window 4*b* in the solid. Upon sonic treatment, the void volume of the first portion 1*a* becomes less than the void volume of the second portion lb. To securely immobilize the sintered polymer during sonic treatment, the article can also include a means for adhering 3 the sintered polymer to the solid.

The article is useful for receiving a liquid sample such as blood, and also body fluids such as serum, plasma, sweat, tears, saliva, semen, cerebrospinal fluid, sputum, urine and cervical mucus or swabbings. The usefulness of the article is enhanced if the surface of the sintered polymer is hydrophilic, for example by being coated with detergent. When the sample to be applied is blood, the sintered polymer can also be treated with a coagulant to remove blood cells from the sample.

When the article is used as a test device for measuring analytes in liquid samples, the article can further comprise a means for reacting 2 with a liquid sample, which can be positioned between the sintered polymer 1 and the window 4*b* of the solid. The reacting means can be a reaction layer containing reagents that can react with specific analytes in the liquid sample. For example, N-ethyl-N-2-hydroxy-3-sulfopropyl-3,5-dimethylaniline (MAOS) reacts with glucose to form a color change, which can be observed by a monitor 5.

The present invention further provides a method for receiving a liquid sample using the article described above.

Under this method, when a liquid sample is applied, the sample is received by the sonically treated polymer 1, migrating preferentially through the second portion 1*b* to reach the reaction layer, rather than spreading laterally to the first portion 1*a*, where it can be retained. As result of this method, less sample is retained in the void volume of the sintered polymer 1, thereby reducing the volume of liquid sample required to use the article.

BRIEF DESCRIPTION OF THE DRAWINGS

FIG. 3A shows the article before sonic treatment. FIG. 3B shows the article after sonic treatment. The arrows represent the general direction and relative volume of migration by a liquid sample applied to the sintered polymer of the assembly.

DETAILED DESCRIPTION OF THE INVENTION

Figure 1:
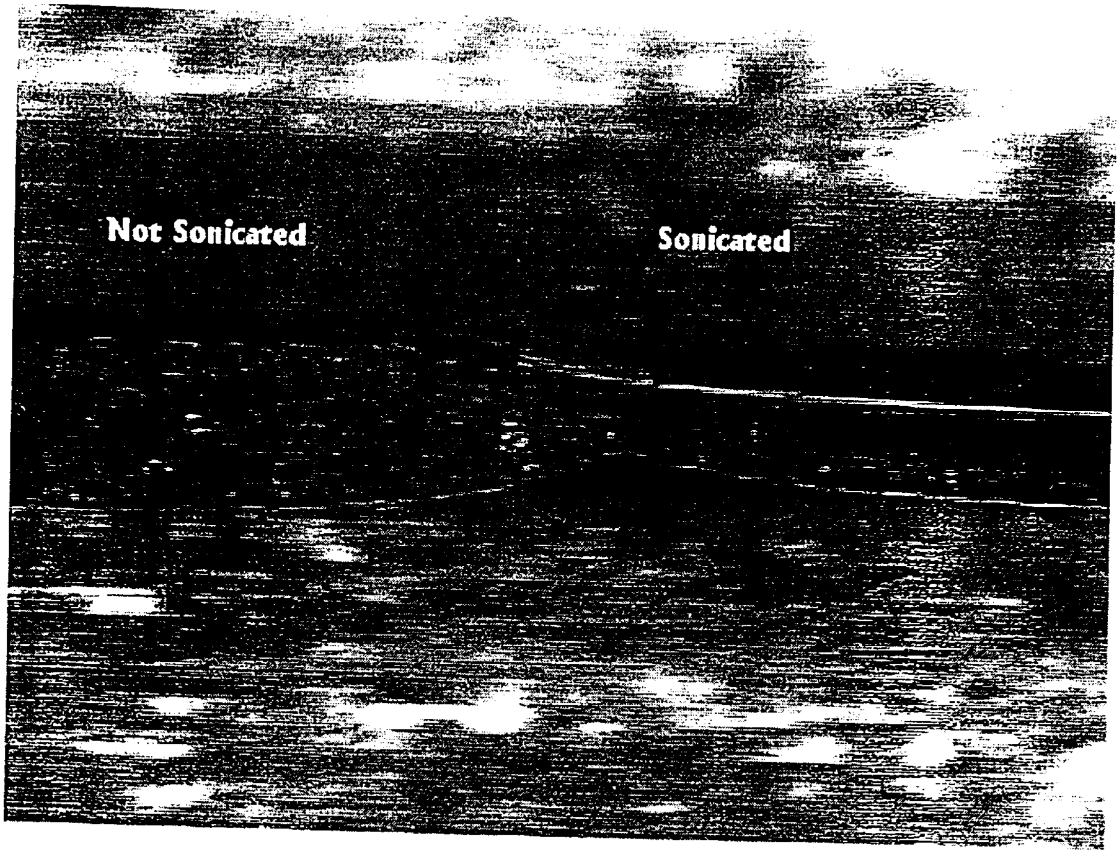
FIG. 1 shows a cross-sectional view of a layer of sintered HDPE. The right side of the HDPE has been sonically treated, while the left side is untreated.

The present invention provides a method of sonic treatment to selectively reduce the void volume of a sintered polymer. A polymer is "sintered" when separate particles of polymer material are partially fused to form a porous mass. Polymer particles are typically sintered by compression or heating without completely crushing or melting the particles. Because the particles are only partially fused, some of the spaces between the individual particles remain after the sintering process. The result is a porous polymer material containing a network of channels (see FIG. 1).

A porous polymer can therefore be useful as a filter to trap fine solid particulates, while allowing liquids and gases to pass through the network of channels. In addition, sintered polymers are useful for wicking and absorbing liquids into the channels of the polymer by capillary action. In these applications, however, the original liquid can never be completely recovered because a certain amount of the liquid is retained in the interconnected channels of the polymer. The volume of liquid that a sintered polymer can absorb into its interconnected spaces is generally related to the void volume. As used herein, the term "void volume" refers to the volume of the spaces between the partially fused particles. Thus, the greater the void volume, the more liquid is retained by the sintered polymer.

For some applications, it is useful to reduce the void volume to minimize the amount of liquid retained in the sintered polymer. When using the polymer to convey a small volume of sample by wicking, for example, it is desirable to recover as much of the sample as possible. As disclosed in the present application, physical disruption of the sintered structure of a polymer can reduce the volume of space between the particles, decreasing the void volume, and thereby minimizing the volume of liquid retained in the sintered polymer (see FIG. 1).

Such disruption is achieved by subjecting the sintered polymer to "sonic treatment," which directs vibrational sound energy at high frequencies against the polymer. The method of the invention therefore reduces the void volume of a sintered polymer by sonically treating its structure, and is useful for controlling the rate of wicking and absorptive properties of the polymer.

Devices for sonic treatment are commercially available, for example from Sonics & Materials, Inc. (Danbury, Conn.), Herrmann Ultrasonics Inc. (Schaumburg, Ill.) and Branson Ultrasonics (Singapore). The Ultra-Com Model 210 from Dukane Ultrasonics (St. Charles, Ill.) is particularly useful. Such devices typically direct the sonic energy to the target via a welding horn applying uniform pressure, for example at 70 or 88 psi.

For the sonic treatment method to be effective, the energy must be sufficiently great to disrupt the structure of the sintered polymer. The amount of energy required is expressed in terms of the amount of sonic energy directed to a given volume of sintered polymer. Thus, the sonic treatment should direct at least 10 Joules per cubic centimeter of sintered polymer (J/cc) to effectively disrupt the sintered structure of a polymer. The sonic treatment is also effective at greater than 20, 50, 100, 200 and 500 J/cc.

However, the sonic energy should not be so great as to melt the sintered polymer or to cause the polymer to become dislodged by the vibrations during treatment. Thus, the sonic treatment per treatment should be less than 1000 J/cc, or alternatively less than 900, 800, 700, 600 or 500 J/cc. For example, when 600 Joules was directed against a 17×1.6 cm area of sintered polymer 0.0635 cm thick, the sonic energy was 347 J/cc, which effectively reduced the void volume of the polymer without melting.

The disruption of a sintered polymer can also be affected by the frequency of the sound waves, which is measured in kilohertz (kHz). However, the frequency of sound waves can vary in actual use, depending on several factors, including the instrument used, damping caused by the target material and fluctuations in the power source. Therefore, the frequency is best described in approximate terms. For example, the frequency of the sonic treatment is effective from a lower range of about 15 to 20 kHz to an upper range of about 40 to 50 kHz. The duration of the sonic treatment can also vary, depending on the energy, frequency and sintered polymer, but is effective when applied for about 0.2, 0.5, 1, 2 or 5 seconds.

Effective conditions for sonic treatment are ascertained by one skilled in the art by testing various parameters on a sintered polymer and determining whether the sonic treatment has physically disrupted the sintered structure of the polymer without melting or dislodging it. Whether the disruption is sufficient to reduce the void volume is readily determined by microscopic inspection, as described in Example I, or by the drop-absorption method provided in Example II. The conditions for sonic treatment will vary, of course, depending on the composition, shape and arrangement of the sintered polymer.

Examples of polymers that are sintered by the method of the invention include polypropylene, polyvinylidene fluoride, ethylenevinyl acetate, styreneacrylonitrite and polytetrafluoroethylene, for example POREX X-4908 sintered polypropylene (Porex Technologies; Fairburn, Ga.). Other useful sintered polymers are obtained by combining or copolymerizing more than one type of polymer material into a copolymer to optimize strength, heat, corrosion or abrasion-resistance properties. For example, POREX X-4105 SCP is a sintered copolymer of 95% polypropylene and 5% polyethylene (Porex Technologies; Fairburn, Ga.).

A useful polymer is sintered polyethylene, which is available as ultra high molecular weight polyethylene, high density polyethylene (HDPE), low density polyethylene or very low density polyethylene (all from GenPore; Reading, Pa.). Particularly useful forms of sintered polyethylene are POREX XM-1342 sintered high density polyethylene, POREX X-4913 sintered high density polyethylene coarse sheet; and POREX X-4908 sintered polypropylene medium sheet and POREX X-4900 sintered ultra high molecular weight polyethylene (all from Porex Technologies; Fairburn, Ga.).

Sintered HDPE and other polymers useful in the invention can have a variety of pore sizes. Pore sizes are described in terms of "effective diameter," which measures the ability of particles of a predetermined diameter to pass through the porous substance, even though the pores and the passages may be irregular. Moreover, because the size of the pores can be nonuniform, they can be described in terms of an average effective pore diameter or as a range of effective pore diameters.

Average pore sizes can be measured on a Mercury Intrusion Porisimeter (Micromeretics; Norcross, Ga.). For example, the sintered HDPE can be extra fine with an average effective diameter of 27 microns; fine with an average effective diameter of 69 microns; medium with an average effective diameter of 119 microns; and coarse with an average effective diameter of 167 microns (available from Porex Technologies as part numbers 4920, 4900, 4903 and 4732, respectively). In terms of a range of effective pore diameters, a particularly useful sintered polymer can have pores of an effective diameter between 5 and 300 microns. Other useful ranges for the effective diameter of pores can have a lower value of 0.5, 1, 2, 10, 25, and 50 microns and an upper value of 20, 50, 100, 500 and 1000 microns.

Because sonic treatment disrupts the sintered structure of a polymer, the pore sizes can also be affected, typically reducing the pore sizes or making the pore size distribution more uniform. Thus, the sonic treatment can also be useful for selectively modifying the pore sizes of the sintered polymer. In particular, sonic treatment can be selectively directed at specific portions of the polymer to reduce the pore sizes of a desired area of the polymer. Thus, a sintered polymer can be sonically treated at different intensities at various portions of the polymer to create a filter with selected pore sizes within the polymer.

For example, a sintered polymer can be sonically treated with more intensity toward the bottom and less intensity at the top, resulting in a gradient filter. The gradient filter will therefore have relatively wide pores at the upper portion and progressively narrower pores toward the bottom. If a sample containing heterogenous particles is applied to the gradient filter, larger particulates are trapped in the upper portion, smaller particulates in the lower portions, and the smallest particulates allowed to pass through the filter. If desired, the filter can then be sliced into sections to retrieve the particulates, sorted according to size. Thus, the sonic treatment of the invention allows pores in a sintered polymer to be selectively manipulated according to size and location within the polymer (see Example II).

As indicated above, the conditions of the sonic treatment can also be affected by the shape of the sintered polymer. Various shapes are useful, such as an elongated form so that the sintered polymer can serve as a slender wick for liquids. The sintered polymer can also be "substantially planar," as in the form of a thin flat sheet. For example, POREX XM-1342 HDPE is supplied in sheets between 0.024 and 0.028 of an inch thick.

When the sonic treatment is directed to a sheet of sintered polymer, it is useful to describe the treatment in terms of amount of sonic energy directed to a given surface area of polymer. Thus, the sonic treatment should direct at least 1 Joule per square centimeter of sintered polymer (J/sc) to effectively disrupt the sintered structure of the polymer. The sonic treatment can also be effective at greater than 2, 5, 10, 20 and 30 J/sc. The sonic treatment per treatment should also be less than 50 J/sc, or alternatively, less than 45, 40, 35 or 30 J/sc. For example, when 600 Joules was directed against a 17×1.6 cm area of sintered polymer in sheet form, the sonic energy was 22 J/sc, which effectively reduced the void volume of the polymer without melting.

The effectiveness of the sonic treatment is enhanced if the sintered polymer is "immobilized" during the sonic treatment: the polymer is fixed to a solid to decrease its ability to vibrate independently of the solid. An immobilized sintered polymer need not be in direct contact with the solid; for example, the sintered polymer can be immobilized to the solid by an adhesive between the polymer and the solid.

By immobilizing the sintered polymer to a solid, the polymer vibrates less during sonic treatment, thereby retaining the sonic energy to disrupt the internal structure of the polymer. When sonic treatment is applied to a sintered polymer that is not securely fixed, however, the sonic energy may cause the polymer to vibrate, dispersing a fraction of the sound energy as kinetic or thermal energy rather than causing the desired disruption of the polymer. Thus, immobilizing or not immobilizing the sintered polymer during sonic treatment can be used to control the level of disruption, consequently controlling the reduction of the void volume in the polymer.

The solid need not be immobilized before or after the sonic treatment. For example, the sintered polymer can be temporarily immobilized against a solid during the sonic treatment by pressing the polymer against a solid surface. After the sonic treatment, the solid surface can be removed so that the polymer is no longer immobilized.

Whether the sintered polymer is immobilized during sonic treatment can also be used to control the reduction of void volume for one portion of the polymer compared to another portion. For example, a first portion of the sintered polymer can be immobilized against a solid during sonic treatment, while a second portion is not. As a result, the void volume in the first portion becomes less than in the second portion. Selective reduction of the void volume in portions of a sintered polymer is illustrated in FIG. 2.

Figure 2:
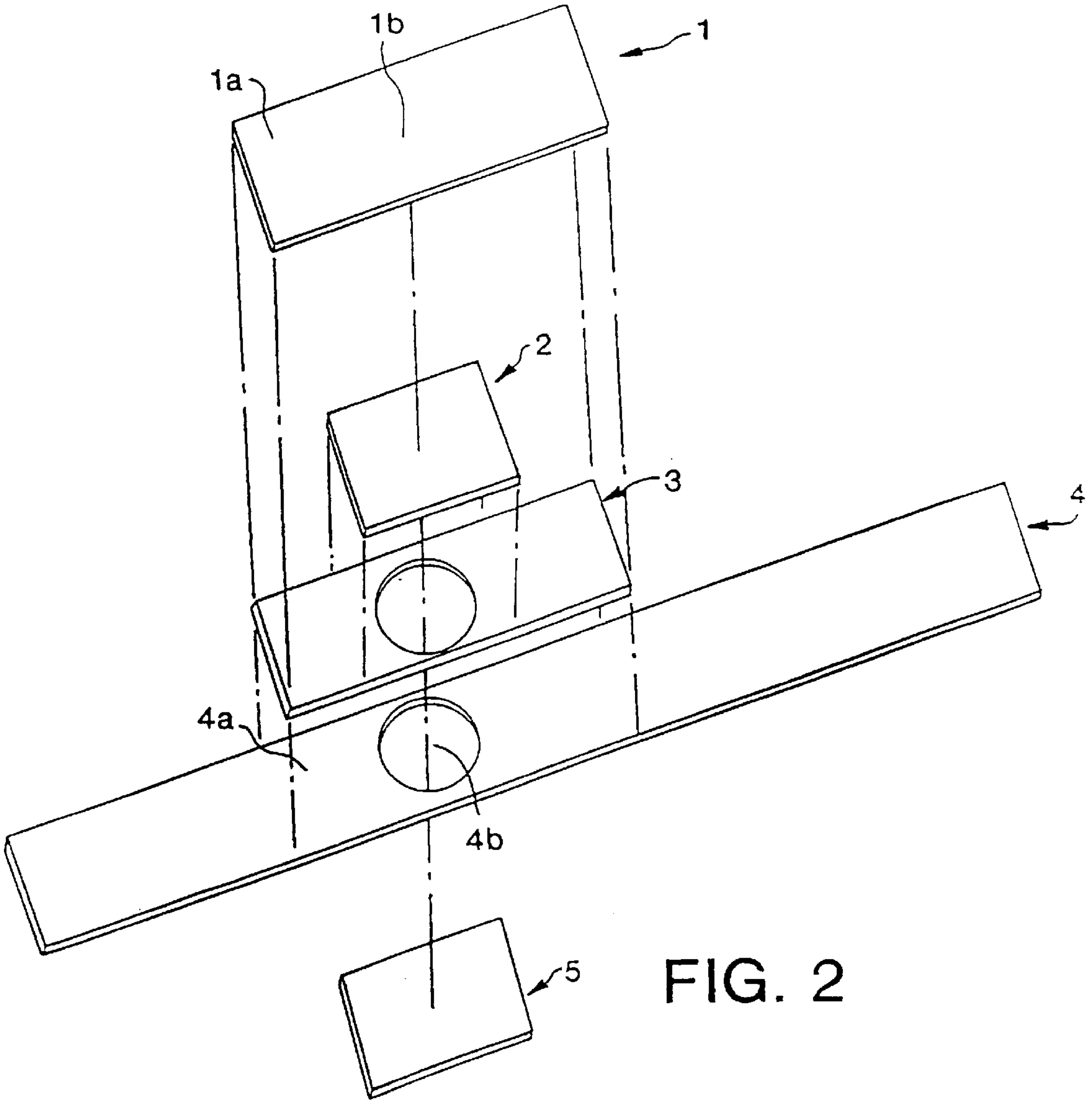
FIG. 2 shows an exploded isometric view of an article of manufacture.

In FIG. 2, a sintered polymer 1 can overlie a solid 4 having a window 4*b*. The "window" 4*b* can be a hole, a recess, a discontinuity or a space between two separate solids—so long as a portion of a solid is not immobilized against a portion of the polymer. A first portion 1*a* of the sintered polymer overlies the portion of the solid without the window 4*a* and a second portion 1*b* overlies the window 4*b* on the solid. When sonic energy is directed to the entire surface of the sintered polymer 1, the first portion of the sintered polymer 1*a* becomes disrupted because it is immobilized against the solid 4*a*. In contrast, the second portion of sintered polymer 1*b* overlies the window 4*b,* which relieves a portion of the sonic energy, so there is less disruption of that portion 1*b* of the sintered polymer. As a result, the sonic treatment disrupts the sintered structure of the first portion 1*a* more than the second portion 1*b,* so that the void volume of the first portion 1*a* is less than the void volume of the second portion 1*b*.

Furthermore, the level of disruption can be manipulated by adjusting the degree of immobilization of the sintered polymer to the solid. For example, complete immobilization of the polymer against a solid maximizes the disruption caused by sonic energy. As discussed above, however, failure to immobilize the polymer results in dispersal of the energy through vibration or heat. However, partial immobilization can be used to obtain intermediate levels of disruption. For example, the gradient filter discussed above can also be obtained by varying the degree of immobilization of a sintered polymer during sonic treatment: not immobilized at an upper portion, moderately immobilized at a middle portion, and strongly immobilized at a bottom portion.

Sonic treatment therefore allows the selection of the shape of the area with reduced void volume. As one example, a sheet of sintered polymer can overlie a solid with an elongated channel. Upon sonic treatment, the portion of the polymer overlying the solid will have reduced void volume, but the portion overlying the channel during sonic treatment will be relatively unaffected. As a result, the sintered polymer will have an elongated track of relatively greater void volume. If a liquid sample is applied to one end of the track, it will migrate preferentially along the track, rather than spread to the sonically treated areas of the polymer, which have reduced void volume.

The shape and number of the tracks can be selected according to the desired application. For example, a Y-shaped track can be obtained by sonically treating a sintered polymer immobilized against a solid mold containing a Y-shaped channel. When a liquid sample is applied to the base of the Y-shaped track after sonic treatment, the sample can migrate upward and be diverted into two separate areas, such as for independent glucose and a fructosamine analyses. Similar methods can be applied to make an article of manufacture to receive a liquid sample.

The present invention also provides an article of manufacture for receiving a liquid sample. The article is useful for providing a receiving layer to quickly absorb a liquid sample, while minimizing the amount of sample retained by the receiving layer.

As shown in FIG. 2, the article comprises a solid 4 having a window 4*a* and a layer of sintered polymer 1, where a first portion 1*a* of the polymer overlies the surface 4*a* of the solid without the window and a second portion 1*b* of the polymer overlies the window 4*b* of the solid. When the sintered polymer is sonically treated, the void volume of the first portion 1*a* becomes less than the void volume of the second portion 1*b*. One embodiment of the example is shown in an exploded view in FIG. 2.

Figure 3A:
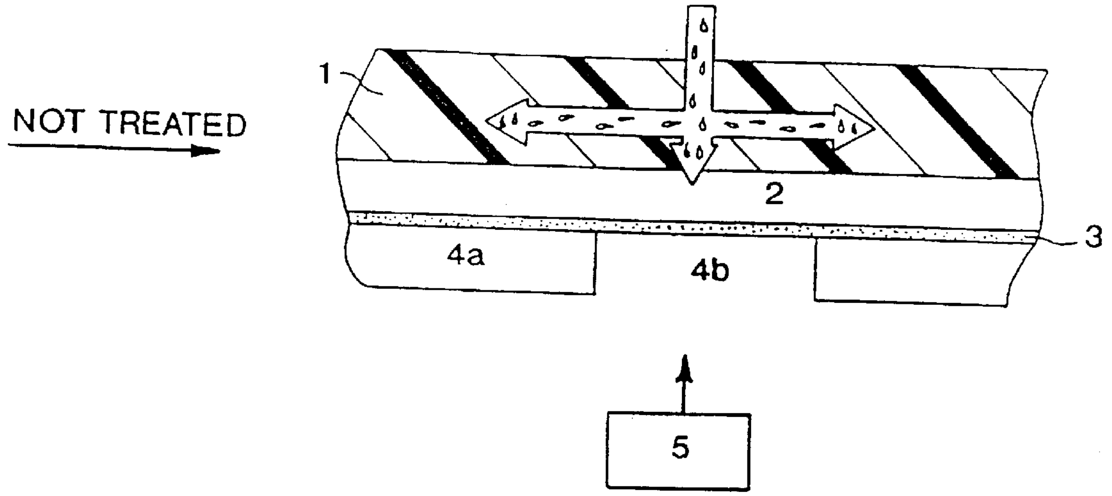
FIGS. 3A and 3B show cross-sectional partial views of an article of manufacture for receiving a liquid sample.
Figure 3B:
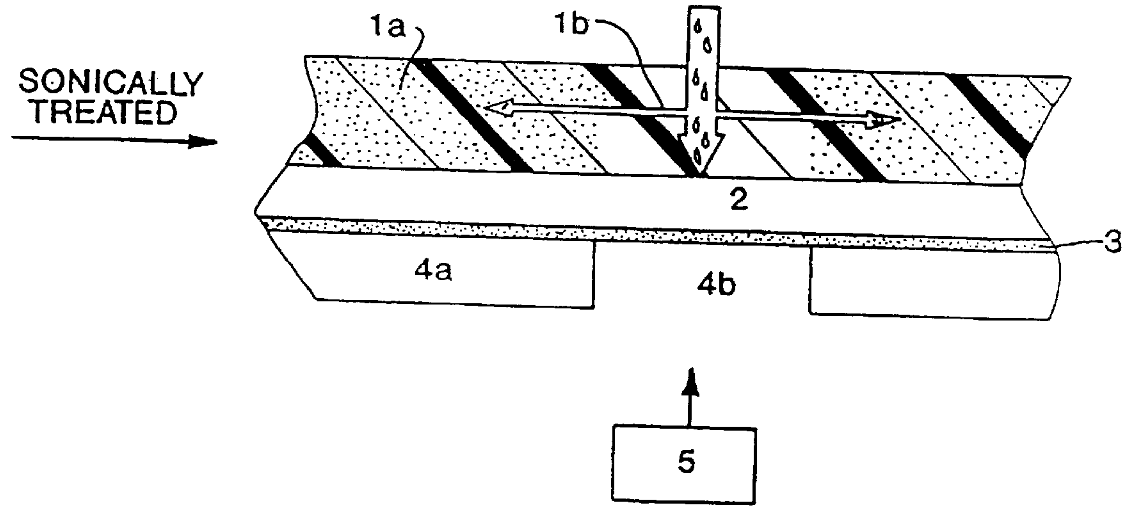

As shown in FIG. 3B, a liquid sample is applied on the upper surface of the sintered polymer 1. Because of the porous structure of the sintered polymer, the liquid is readily absorbed into the interconnected spaces of the polymer (see Example II). As the liquid is absorbed, it migrates by capillary action through the sintered polymer material. The capillary action is more rapid where the void volume is greater within the sintered polymer. Thus, where one portion of the sintered polymer has selectively reduced void volume relative to another, the liquid will tend not to migrate through the portion with reduced void volume. Consequently, sonic treatment allows the liquid preferentially migrates through the second portion of the polymer and more sample will migrate downward toward the window 4*b*.

In an untreated article, as shown in FIG. 3B, the void volume is the same throughout the sintered polymer, as depicted in FIG. 3A. As before, when a liquid sample is applied to the untreated article, the sample migrates downward toward the window 4*b*. However, a significant fraction of the sample tends to spread laterally through the sintered polymer, where it is retained in the periphery of the polymer 1*b*. Therefore, in applications where sample migration toward the window is desirable, less sample need be applied to sonically treated articles than untreated articles to obtain equivalent volumes of sample migrating toward the window 4*b*.

The article can also comprise a "means for adhering" the sintered polymer to the solid. For example, the adhering means can be acrylic-, rubber- or silicone-based adhesives. A particularly useful acrylic-based adhesive layer is FASTAPE 8311 double-coated acrylic-based adhesive (Avery-Dennison, Inc.; Pasadena, Calif.). Other adhesives include 3M 444 or 3M 415 double-coated adhesives (3M; Minneapolis, Minn.). Means for adhering the sintered polymer to the solid can also include PVC plastic pipe cement, epoxy, heat staking, clamping, bolting, nailing, compression fitting and immobilization by vacuum. The positioning of the adhering means is not critical as long as the sintered polymer is securely fixed to the solid.

In FIG. 2, for example, a adhering means has been incorporated into the assembly as a adhesive layer 3 between the sintered polymer 1 and the solid support 4. When an adhesive layer is present, the sonic treatment has the further benefit of welding a tight seal between the sintered polymer, the adhesive layer and the solid. The tight seal ensures that the article remains assembled when used to receive a liquid sample.

The "liquid sample" to be applied to the sintered polymer encompasses any fluid containing an analyte to be measured. For example, the term encompasses blood, serum or plasma. The term also encompasses other patient specimens such as sweat, tears, saliva, semen, cerebrospinal fluid, sputum, urine and cervical mucus or swabbings. The term further encompasses food, environmental or industrial samples, depending on the desired application of the article, as long as they are liquid and contain an analyte for measurement.

The liquid sample can be analyzed for specific analytes, which is any substance to be detected or quantitated in terms of concentration. For example, the analyte can be glucose, fructose, or other sugars, cholesterol, ketones, lipids, uric acid or specific amino acids such as phenylalanine. The analyte can also be proteins, for example enzymes such as amylase, creatine kinase or alanine aminotransferase. Furthermore, the analyte can be glycated proteins, for example serum or plasma glycated protein as measured by fructosamine, or red blood cell glycated protein as measured by glycated hemoglobin, in particular $Hb_{A1C}$. Other analytes are described in U.S. Pat. No. 5,597,532, incorporated herein by reference.

When used as a test strip device to receive and analyte liquid samples, the article is particularly effective when the surfaces of the sintered polymer are hydrophilic so that the polymer can readily wick the liquid sample. If the sintered polymer composition itself is not inherently hydrophilic, the polymer can be rendered hydrophilic by incorporating hydrophilic or amphipathic components into the composition before sintering. For example, the surfactant ethanesulfonic acid 2-(methyl(1-oxo-9-octadecenyl)amino), sodium salt can be incorporated into polyethylene so that the final sintered product is hydrophilic.

After a polymer is sintered, it can also be treated with a "coating" so that a layer of detergent covers the outside surfaces as well as the surfaces within the sintered structure of the polymer, rendering the polymer more hydrophilic. For example, sintered HDPE can be treated with a detergent such as polyoxypropylene polyoxyethylene block copolymer (Pragmatics Inc.; Oak Ridge, Tenn.) or MAPHOS 66 phosphate esters (Mazer Chemical; Gurnee, Ill.). A particularly useful treatment is soaking sintered HDPE in an aqueous solution of 20% isopropanol and 0.03% TWEEN-20 polyoxyethylene(20)sorbitan monolaurate (Calbiochem; La Jolla, Calif.).

When the liquid sample to be applied to the article is blood, the sintered polymer can be further treated with a coagulant to remove blood cells from the sample. As used herein, a "coagulant" is a material that causes a homogenous suspension of particle, such as red blood cells, to agglomerate into larger masses, which can be removed by settling or filtration. For example, the sintered polymer can be coated using a solution containing 0.15% hexadimethrin in a 0.85% NaCl solution. The use of coagulants to confer blood-separation properties to such polymers is disclosed in greater detail in U.S. patent application Ser. No. 08/418,523, filed Apr. 7, 1995, published as PCT WO 96/31270, incorporated herein by reference. Other coagulants useful in the invention include anti-thrombin III, factor V, factor VII, human factor IX, human factor X, human fibrogen, fibrogen from whole serum, human protein C, human protein C alkaline phosphatase conjugate, human beta-protein C, human protein S and human von Willebrand factor.

When used in a test strip device, the article can further comprise a "means for reacting" with a liquid sample: a means that can react with specific analytes in a liquid sample. A representative means for reacting with glucose is the reaction layer disclosed in Example III, which is a porous nylon membrane treated with reactants. Other representative reaction layers are described in U.S. Pat. No. 5,470,752, U.S. Pat. No. 5,597,532 and U.S. Pat. No. 5,695,949, each incorporated herein by reference. Another type of means for reacting with the liquid sample is a layer that can result in a detectable electrochemical change upon reaction with the liquid sample. Such means are described in U.S. Pat. No. 5,639,672, incorporated herein by reference.

As exemplified in FIG. 3A, a reacting means is incorporated into the assembly as a reaction layer 2 between the sintered polymer 1 and the solid support 4. In this position, a liquid sample applied to the sintered polymer 1 will migrate preferentially through the second portion 1*b* of the polymer until it reaches the reaction layer 2, allowing the sample to react with any reactants present on the reaction layer. The reacting means need not be positioned between the sintered polymer and the solid support, however. For example, the reacting means can be positioned below the solid 4, as long as the liquid sample can migrate to the reaction layer and any resulting reaction is observed.

A particularly useful reaction layer contains a reagent that reacts with glucose in the liquid sample. Typical reagents for reacting with glucose include N-ethyl-N-2-hydroxy-3-sulfopropyl-3,5-dimethylaniline (MAOS) and N-ethyl-N-(2-hydroxy-3-sulfopropyl)-m-toluidine (TOOS). Other reagents include the combination of 4-aminoantipyrene and chromotropic acid (AAP-CTA) and the combination of 3-methyl-2-benzothiazoline hydrazone hydrochloride (MBTH) and either 3-dimethylaminobenzoic acid (DMAB) or 8-anilo-1-napthalenesulfonate (ANS). These reagents can react with glucose present in the liquid sample to cause a color reaction that is detected by a reflectance monitor 5 positioned under the window 4*b*. In this position, the monitor can detect changes on the reaction layer 1 through the window 4*b*. Monitors useful in the invention are disclosed in further detail in U.S. patent application Ser. No. 08/842,616, filed Apr. 15, 1997, incorporated herein by reference.

Finally, the present invention provides a method for receiving a liquid sample. By applying a liquid sample to the article described above, the sample preferentially migrates through the sintered polymer toward the window, rather than spreading to peripheral areas of the sintered polymer having a reduced void volume. Consequently, less sample need be applied to obtain the desired volume of sample from the sintered polymer (see Example III).

The following examples are intended to illustrate but not limit the present invention.

EXAMPLE I

Sonic Treatment of a Sintered Polymer

The following example shows that sonic treatment disrupts the structure of a sintered polymer. The photograph in FIG. 1 shows a microscopic cross-section at 40× magnification of POREX XM-1342 sintered high density polyethylene (HDPE) (Porex Technologies; Fairburn, Ga.). The HDPE was supplied in sheets 0.0635 cm thick.

A portion of the HDPE was then sonically treated as follows. A Dukane Ultrasonics welding press (St. Charles, Ill.) was used, having a 6.75"×0.625" (17.1 cm×1.6 cm) welding horn. The welding horn pressed against the HDPE at 88 psi. The welding press then directed 1200 Joules of sonic energy for 1 second at 20 kilohertz to the 6.75"×0.625" area under the welding horn, resulting in sonic treatment of 559 J/cc.

The photograph in FIG. 1 shows a microscopic cross-section of a layer of sintered HDPE. The right side of the HDPE has been sonically treated, while the left side is not treated. As shown, the sonic treatment has disrupted the sintered structure of the right side of the HDPE, compared to the untreated left side. As a result, the volume of the interconnected spaces between the individual sintered particles is decreased. Thus, sonic treatment is effective for reducing the void volume of the sintered polymers.

As a further result of sonic treatment, the thickness of the HDPE is visibly reduced, thereby increasing the density of the HDPE layer. Sintered HDPE was previously considered a relatively noncompressible layer that returns to its original thickness after compression. Thus, the sonic treatment method is also useful for compressing a sintered polymer such as HDPE.

EXAMPLE II

Detection of Reduced Void Volume by Drop-Absorption

Reduction in void volume can also be demonstrated by measuring the time required for a sintered polymer to absorb a given volume of liquid. A sintered polymer that has reduced void volume will not absorb a liquid sample as readily as an untreated polymer because the sintered structure of the treated polymer has been disrupted by sonic energy.

Five different types of sintered polymer were tested: POREX XM-1342 sintered high density polyethylene; POREX X-4105 SCP sintered co-polymer sheet; POREX X-4900 sintered ultra high molecular weight polyethylene, 15 to 45 micron pore size; POREX X-4913 sintered high density polyethylene coarse sheet, 90 to 130 micron pore size; and POREX X-4908 sintered polypropylene medium sheet, 120 micron average pore size (all from Porex Technologies; Fairburn, Ga.).

The sintered polymers were sonically treated as follows. A Dukane Ultrasonics welding press (St. Charles, Ill.) was used, with the welding horn pressed against the sintered polymer at 88 psi. The welding press then directed sonic energy for 1 second at 20 kilohertz, resulting in sonic treatment of 559 J/cc. The energy of the sonic treatment was varied from 0 J, as a control, to 1200 J.

A 20 microliter sample of blood, treated with tripotassium ethylenediaminetetraacetate (EDTA) as an anticoagulant, was then applied to the surface of the sintered polymer using a micropipet. The time required for the sintered polymer to absorb the sample was measured by a digital stopwatch. The results shown below are the averages of 5 experiments for each energy level.

POREX XM-1342 sintered high density polyethylene:

| Sonic energy | Seconds to absorb |
|---|---|
| 0 J = 0 J/cc | 0.358 |
| 300 J = 174 J/cc | 0.634 |
| 600 J = 348 J/cc | 0.836 |
| 900 J = 521 J/cc | 1.084 |
| 1200 J = 695 J/cc | 2.038 |

POREX X-4105 SCP sintered co-polymer sheet:

| Sonic energy | Seconds to absorb |
|---|---|
| 0 J = 0 J/cc | 0.545 |
| 1200 J = 695 J/cc | 1.956 |

POREX X-4900 sintered ultra high mol. wt. polyethylene:

| Sonic energy | Seconds to absorb |
|---|---|
| 0 J = 0 J/cc | 0.569 |
| 1200 J = 695 J/cc | 1.065 |

POREX X-4913 high density polyethylene coarse sheet:

| Sonic energy | Seconds to absorb |
|---|---|
| 0 J = 0 J/cc | 0.468 |
| 1200 J = 695 J/cc | 1.547 |

POREX X-4908 sintered polypropylene medium sheet:

| Sonic energy | Seconds to absorb |
|---|---|
| 0 J = 0 J/cc | 0.300 |
| 1200 J = 695 J/cc | 0.563 |

These results demonstrate that sonic treatment slows the ability of various sintered polymers to absorb a liquid sample. As shown below, the ability to selectively slow absorption of a liquid is used to control the volume and direction of flow of a liquid sample in a test strip device.

EXAMPLE II

Sonic Treatment of a Sintered Polymer in a Test Strip Device

This example describes the sonic treatment of a sintered polymer incorporated into a test strip assembly. As disclosed below, sonic treatment of the test strip assembly reduces the void volume of the sintered polymer, and consequently the volume of liquid sample needed to be applied to the assembly.

This example describes a test strip assembly incorporating sintered HDPE. A solid polyester support 4 having a circular window 4*b* was used as a solid base for the assembly. A layer of FAS-TAPE 8311 double-coated acrylic-based adhesive 3 (Avery-Dennison, Inc.; Pasadena, Calif.) was applied to the support 4 around the area of the window 4*a*. A reaction layer 2 of BIODYNE A 0.65 μm pore size nylon membrane (Pall Corp.; East Hills, N.Y.) was then positioned on the support 4 over the window, but not completely covering the adhesive layer 3. The reaction layer was impregnated with a glucose oxidase/horseradish peroxidase system (Toyobo Inc.; Tokyo, Japan) and MAOS (N-ethyl-N-2-hydroxy-3-sulfopropyl-3,5-dimethylaniline, sodium salt, monohydrate) (Dojindo Laboratories; Kumamoto, Japan).

Finally, a layer of hydrophilic POREX XM-1342 sintered high density polyethylene (HDPE) 1 was positioned over the reaction layer 2, completely covering the reaction layer and in contact with the adhesive layer 3. The HDPE had been previously treated with between 0.0001% and 0.1% PLURONIC polyoxypropylene polyoxyethylene block copolymer (Pragmatics Inc.; Oak Ridge, Tenn.), 8% mannitol, and 0.15% hexadimethrin, all in a 0.85% NaCl solution.

The assemblies were then sonically treated as described in Example I, except at 70 psi and 200 Joules of energy, effectively welding the assembly together. Control assemblies were pressed at 70 psi, but were not subjected to sonic treatment.

The assemblies were tested for their ability to receive a liquid sample and allow the sample to migrate through the HDPE and reach the reaction layer. Failure of a sample to reach the reaction layer indicated that a significant portion of the sample had been retained in the HDPE layer. As disclosed above, such retention can result from lateral spreading of the sample to the periphery of the HDPE. Lateral spreading is reduced, however, by sonic treatment to reduce the void volume of selected portions of the HDPE. Consequently, the assemblies were tested for selectively reduced void volume by testing whether a liquid sample was sufficient to successfully wet the underlying reaction layer.

Blood samples in volumes of 5 and 10 microliters were applied to the HDPE layer in 10 treated and 10 untreated assemblies each. Whether the sample migrated through the HDPE to the underlying reaction layer was determined by whether the reaction layer became wetted by the liquid sample. Wetting was detected by measuring a predetermined change in the reflectance of the strip, indicating that the sample has wetted the strip.

Changes in reflectance were detected by directing 635 nm light from a light-emitting diode through the window to the reaction layer surface. Changes in the level of diffuse reflected light back through the window were then detected by a silicon photodiode to indicate wetting of the reaction layer.

The results were as follows:

| volume of sample applied wetted | sonic treatment | fraction of assemblies where the strip was |
|---|---|---|
| 5 μl | no | 0/10 = 0% |
| 10 μl | no | 1/10 = 10% |
| 5 μl | yes | 10/10 = 100% |
| 10 μl | yes | 10/10 = 100% |

As shown by the results, 5 and 10 μl samples were sufficient to wet the reaction layers in all the sonically treated assemblies, but almost none of the untreated assemblies. Accordingly, sonic treatment enables the reaction layer in such assemblies to be reliably wetted with 10 μl or even 5 μl of sample.

Thus, sonic treatment of sintered polymers used in assemblies reduces the volume of liquid sample necessary to wet the reaction layer, demonstrating that the void volume was selectively reduced in the sonically treated HDPE.

We claim:

1. An article of manufacture for receiving a liquid sample, comprising a solid having a window and a sintered polymer, wherein a first portion of the polymer overlies the window and a second portion of the polymer overlies the surface of the solid without the window; and wherein the polymer is sonically treated; whereby the void volume in the first portion is less than the void volume in the second portion.

2. The article of claim 1, further comprising a means for adhering the sintered polymer to the solid.

3. The article of claim 1, wherein the liquid sample is selected from the group consisting of blood, serum, plasma, sweat, tears, saliva, semen, cerebrospinal fluid, sputum, urine and cervical mucus or swabbings.

4. The article of claim 3, wherein the liquid sample is blood.

5. The article of claim 1, wherein the surface of the sintered polymer is hydrophilic.

6. The article of claim 1, wherein the sintered polymer further comprises a coating of detergent.

7. The article of claim 6, wherein the sintered polymer further comprises a coagulant.

8. The article of claim 1, further comprising a means for reacting with a liquid sample.

9. The article of claim 8, wherein the reacting means is positioned between the sintered polymer and the window of the solid.

10. The article of claim 8, wherein the means for reacting is a reaction layer.

11. The article of claim 10, wherein the reaction layer comprises a reagent that reacts with glucose.

12. The article of claim 11, wherein the reagent is N-ethyl-N-2-hydroxy-3-sulfopropyl-3,5-dimethylaniline (MAOS).

13. A method for receiving a liquid sample, comprising the steps of applying a liquid sample to an article of claim 1 on the side of the sintered polymer opposite the window and allowing the sample to migrate toward the window, whereby the sample does not migrate away from the window due to the reduced void volume in the first portion.

* * * * *